US011160833B2

(12) United States Patent
Chen et al.

(10) Patent No.: US 11,160,833 B2
(45) Date of Patent: Nov. 2, 2021

(54) BISPECIFIC OR-GATE CHIMERIC ANTIGEN RECEPTOR RESPONSIVE TO CD19 AND CD20

(71) Applicants: The Regents of the University of California, Oakland, CA (US); Seattle Children's Hospital, Seattle, WA (US)

(72) Inventors: Yvonne Y. Chen, Los Angeles, CA (US); Eugenia Zah, Los Angeles, CA (US); Michael C. Jensen, Seattle, WA (US)

(73) Assignees: The Regents of the University of California, Oakland, CA (US); Seattle Children's Hospital, Seattle, WA (US)

( * ) Notice: Subject to any disclaimer, the term of this patent is extended or adjusted under 35 U.S.C. 154(b) by 0 days.

(21) Appl. No.: 17/028,701

(22) Filed: Sep. 22, 2020

(65) Prior Publication Data

US 2021/0145880 A1 May 20, 2021

Related U.S. Application Data

(62) Division of application No. 15/535,972, filed as application No. PCT/US2015/065620 on Dec. 14, 2015.

(60) Provisional application No. 62/091,854, filed on Dec. 15, 2014.

(51) Int. Cl.
| | | |
|---|---|---|
| *C07K 16/00* | (2006.01) | |
| *C12P 21/08* | (2006.01) | |
| *G01N 33/53* | (2006.01) | |
| *G01N 33/567* | (2006.01) | |
| *C12N 5/00* | (2006.01) | |
| *C12N 5/16* | (2006.01) | |
| *A61K 35/17* | (2015.01) | |
| *C07K 16/46* | (2006.01) | |
| *C12N 5/0783* | (2010.01) | |
| *C07K 16/28* | (2006.01) | |
| *C07K 14/725* | (2006.01) | |
| *C07K 14/705* | (2006.01) | |
| *C07K 1/00* | (2006.01) | |
| *A61K 38/00* | (2006.01) | |
| *A61K 39/00* | (2006.01) | |

(52) U.S. Cl.
CPC .......... *A61K 35/17* (2013.01); *C07K 14/7051* (2013.01); *C07K 14/70521* (2013.01); *C07K 14/70596* (2013.01); *C07K 16/2803* (2013.01); *C07K 16/2887* (2013.01); *C07K 16/46* (2013.01); *C12N 5/0636* (2013.01); *A61K 38/00* (2013.01); *A61K 2039/505* (2013.01); *C07K 2317/31* (2013.01); *C07K 2317/622* (2013.01); *C07K 2319/03* (2013.01); *C07K 2319/40* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,797,368 | A | 1/1989 | Carter et al. |
| 5,139,941 | A | 8/1992 | Muzyczka |
| 5,821,337 | A | 10/1998 | Carter et al. |
| 6,319,494 | B1 | 11/2001 | Capon et al. |
| 7,741,465 | B1 | 6/2010 | Eshhar et al. |
| 8,399,645 | B2 | 3/2013 | Campana et al. |
| 9,447,194 | B2 | 9/2016 | Jensen |
| 9,464,140 | B2 | 10/2016 | June et al. |
| 9,518,123 | B2 | 12/2016 | June et al. |
| 9,540,445 | B2 | 1/2017 | June et al. |
| 9,834,590 | B2 | 12/2017 | Campana et al. |
| 2010/0330676 | A1 | 12/2010 | Horowitz et al. |
| 2013/0280220 | A1 | 10/2013 | Ahmed et al. |
| 2014/0141000 | A1 | 5/2014 | Chiu et al. |

FOREIGN PATENT DOCUMENTS

WO   WO 2013/123061   8/2013

OTHER PUBLICATIONS

Ahmad et al., "scFv Antibody: Principles and Clinical Application," *Clin Dev Immunol*, 2012:980250, (2012).
Boissel et al., "Retargeting NK-92 cells bty means of CD19-and CD20-specific chemieric antigen receptors compares favorably with antibody-dependent cellular cytotoxicity," *OncoImmunology*, 2(10):e26527, (2013).
Budde et al., "Combining a CD20 chimeric antigen receptor and an inducible caspase 9 suicide switch to improve the efficacy and safety of T cell adoptive immunotherapy for lymphoma," *PloS One*, 8(12): e82742, (2013.
Chen et al, "Fusion protein linkers: Property, design and functionality", Advanced Drug Delivery Reviews, vol. 65, (2003), pp. 1357-1369.
Dull et al., "A Third-Generataion Lentivirus Vector with a Conditional Packaging System," *J. Virol*, 72(11):8463-8471, (1998).
International Search Report and Written Opinion Issued in International Application No. PCT/US2015/065620, dated Mar. 28, 2016.
Le Gall et al., "Effect of linker sequences between the antibody variable domains on the formation, stability and biological activity of a bispecific tandem diabody" *Protein Engineering, Design & Selection* 2004, 17(4), 357-366.

(Continued)

*Primary Examiner* — Chun W Dahle
(74) *Attorney, Agent, or Firm* — Norton Rose Fulbright US LLP

(57) ABSTRACT

A CD19-OR-CD20 chimeric antigen receptor (CAR) protein construct is provided. Also provided are nucleic acids encoding the CD19-OR-CD20 CAR; and methods of use, e.g. in the treatment of B cell malignancies. The CD19-OR-CD20 CAR of the invention is a bispecific CAR that can trigger T-cell activation upon detection of either CD19 or CD20 (or both). It is a single molecule that confers two-input recognition capability upon human T cells engineered to stably express this CAR.

10 Claims, 6 Drawing Sheets

Specification includes a Sequence Listing.

(56) References Cited

OTHER PUBLICATIONS

Le Gall et al., "Immunosuppressive properties of anti-CD3 single-chain Fv and diabody" *Journal of Immunological Methods* 2004, 285, 111-127.
Qin et al, "Preclinical Development of Bivalent Chimeric Antigen Receptors Targeting Both CD19 and CD22", *Molecular Therapy: Oncolytics*, vol. 11, Dec. 21, 2018, pp. 127-137.
Qin et al, "Supplemental Information. Preclinical Development of Bivalent Chimeric Antigen Receptors Targeting Both CD19 and CD22", *Molecular Therapy: Oncolytics*, vol. 11.
Stone et al., "A sensitivity scale for targeting T cells with chimeric antigen receptors (CARs) and bispecific T-cell engagers (BiTEs)" *Oncoimmunology*, 1(6):863-873, (2012).
Supplementary European Search Report issued in European Patent Application No. 15870818, dated Apr. 10, 2018.
Szymczak-Workman et al., "Design and construction of 2A peptide-linked multicistronic vectors," *Cold Spring Harb Protoc*, 2012(2):199-204, (2012).

SEQUENCE LISTING

```
<160> NUMBER OF SEQ ID NOS: 13

<210> SEQ ID NO 1
<211> LENGTH: 5
<212> TYPE: PRT
<213> ORGANISM: Homo sapiens

<400> SEQUENCE: 1

Glu Ala Ala Ala Lys
1               5

<210> SEQ ID NO 2
<211> LENGTH: 20
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 246
<212> TYPE: PRT
<213> ORGANISM: Homo sapiens
```

-continued

```
<400> SEQUENCE: 3

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Ser Thr Ser Gly Gly
            100                 105                 110

Gly Ser Gly Gly Gly Ser Gly Gly Gly Ser Ser Glu Val Gln Leu
            115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser
                245

<210> SEQ ID NO 4
<211> LENGTH: 245
<212> TYPE: PRT
<213> ORGANISM: Homo sapiens

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110
```

```
Ser Gly Lys Pro Gly Ser Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 5
<211> LENGTH: 12
<212> TYPE: PRT
<213> ORGANISM: Homo sapiens

<400> SEQUENCE: 5

Glu Ser Lys Tyr Gly Pro Pro Cys Pro Pro Cys Pro
1               5                   10

<210> SEQ ID NO 6
<211> LENGTH: 28
<212> TYPE: PRT
<213> ORGANISM: Homo sapiens

<400> SEQUENCE: 6

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 7
<211> LENGTH: 41
<212> TYPE: PRT
<213> ORGANISM: Homo sapiens

<400> SEQUENCE: 7

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 8
<211> LENGTH: 42
<212> TYPE: PRT
<213> ORGANISM: Homo sapiens
```

```
<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 9
<211> LENGTH: 112
<212> TYPE: PRT
<213> ORGANISM: Homo sapiens

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 24
<212> TYPE: PRT
<213> ORGANISM: Homo sapiens

<400> SEQUENCE: 10

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 11
<211> LENGTH: 110
<212> TYPE: PRT
<213> ORGANISM: Homo sapiens

<400> SEQUENCE: 11

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80
```

-continued

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys
            100                 105                 110

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 357
<212> TYPE: PRT
<213> ORGANISM: Homo sapiens

<400> SEQUENCE: 13

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

-continued

```
Gln Val Cys His Ala Leu Cys Ser Pro Glu Gly Cys Trp Gly Pro Glu
    195                 200                 205
Pro Arg Asp Cys Val Ser Cys Arg Asn Val Ser Arg Gly Arg Glu Cys
    210                 215                 220
Val Asp Lys Cys Asn Leu Leu Glu Gly Glu Pro Arg Glu Phe Val Glu
225                 230                 235                 240
Asn Ser Glu Cys Ile Gln Cys His Pro Glu Cys Leu Pro Gln Ala Met
                245                 250                 255
Asn Ile Thr Cys Thr Gly Arg Gly Pro Asp Asn Cys Ile Gln Cys Ala
            260                 265                 270
His Tyr Ile Asp Gly Pro His Cys Val Lys Thr Cys Pro Ala Gly Val
        275                 280                 285
Met Gly Glu Asn Asn Thr Leu Val Trp Lys Tyr Ala Asp Ala Gly His
    290                 295                 300
Val Cys His Leu Cys His Pro Asn Cys Thr Tyr Gly Cys Thr Gly Pro
305                 310                 315                 320
Gly Leu Glu Gly Cys Pro Thr Asn Gly Pro Lys Ile Pro Ser Ile Ala
                325                 330                 335
Thr Gly Met Val Gly Ala Leu Leu Leu Leu Leu Val Val Ala Leu Gly
            340                 345                 350
Ile Gly Leu Phe Met
        355
```

BISPECIFIC OR-GATE CHIMERIC ANTIGEN RECEPTOR RESPONSIVE TO CD19 AND CD20

CROSS REFERENCE TO RELATED APPLICATIONS

This application is a divisional application of U.S. patent application Ser. No. 15/535,972, filed on Jun. 14, 2017, which is a national phase application under 35 U.S.C. § 371 of International Application No. PCT/US2015/065620, filed Dec. 14, 2015, which claims the benefit of U.S. Provisional Application No. 62/091,854, filed Dec. 15, 2014, the contents of which applications are incorporated into the present application by reference.

GOVERNMENT SUPPORT

This invention was made with Government support under OD012133, awarded by the National Institutes of Health. The Government has certain rights in the invention. This work was supported by the U.S. Department of Veterans Affairs, and the Federal Government has certain rights in the invention.

BACKGROUND OF THE INVENTION

Chimeric antigen receptors (CARs) are artificial molecules that redirect the specificity of T cells to predetermined antigens. These receptors are frequently used to graft the specificity of a monoclonal antibody onto a T cell; with transfer of their coding sequence facilitated by retroviral or lentiviral vectors. Using adoptive transfer, autologous T cells can be genetically modified ex vivo to express a CAR specific for a cancer cell of interest. The T cells, which can then recognize and kill the cancer cells, are reintroduced into the patient. Phase I clinical studies of this approach have shown efficacy.

The most common form of CARs are fusions of single-chain variable fragments (scFv) derived from monoclonal antibodies, fused to CD3-zeta signaling domain, which contains 3 ITAMs. CD3-zeta may not provide a fully competent activation signal and additional co-stimulatory signaling is needed. For example, chimeric CD28 and OX40 can be used with CD3-Zeta to transmit a proliferative/survival signal, or all three can be used together. Such molecules result in the transmission of a zeta signal in response to recognition by the scFv of its target.

Multiple clinical trials have reported remarkable therapeutic efficacy of anti-CD19 CAR-modified T cells against both acute and chronic B-cell malignancies. However, multiple cases have also been reported of patients relapsing with the emergence of CD19-negative leukemia or lymphoma (Maude et al. 2014). This problem of antigen escape, i.e., tumor cells evading treatment by losing the antigen targeted by the T-cell therapeutic, is addressed by this invention.

SUMMARY OF THE INVENTION

CD20 and CD19 are both pan-B-cell markers present on the vast majority of malignant B cells. An OR-gate CAR that triggers tumor killing as long as either CD20 or CD19 is present reduces the probability of antigen escape, by requiring that tumor cells lose both antigens to escape targeting, an event that happens with a significantly lower probability than single-antigen mutations. Therefore, this invention has a strong competitive advantage compared to the conventional, single-input anti-CD19 CAR T-cell therapy.

A CD19-OR-CD20 chimeric antigen receptor (CAR) protein construct is provided. Also provided are nucleic acids encoding the CD19-OR-CD20 CAR; and methods of use, e.g. in the treatment of B cell malignancies. The CD19-OR-CD20 CAR of the invention is a bispecific CAR that can trigger T-cell activation upon detection of either CD19 or CD20 (or both). It is a single molecule that confers two-input recognition capability upon human T cells engineered to stably express this CAR. The CD19-OR-CD20 CAR consists of the following (from N- to C-terminus): signal sequence; anti CD20 scFv; linker; anti-CD19 scFv; spacer domain; transmembrane domain; zero, one, or more cytoplasmic co-stimulatory signaling domains; CD3 zeta signaling domain. In some embodiments the spacer domain is an immunoglobulin hinge domain, including without limitation the human IgG4 hinge.

In some embodiments the transmembrane domain is CD28 transmembrane domain. In some embodiments the cytoplasmic co-stimulatory signaling domain is CD28 and/or 4-1BB. In some embodiment the construct further comprises T2A ribosomal skipping peptide, which can be used to link the CAR to a protein or peptide of interest, e.g. an epitope tag. In some embodiment a sortable tag is included, e.g. truncated epidermal growth factor receptor (EGFRt) or fluorescent proteins, which can be used to separate T cells expressing the CAR.

In some specific embodiments the linker joining the two scFv sequences is a rigid linker. In some specific embodiments, a rigid linker has the sequence SEQ ID NO:1 (EAAAK)n, where n is 1, 2, 3, 4, 5, 6, etc. In some specific embodiments, n is 3.

In some embodiments the CAR construct is packaged into a lentiviral vector, which includes, without limitation, a third-generation lentiviral vector. Primary human T cells can be lentivirally transduced to stably integrate and express the OR-gate CAR. CAR-expressing cells can be enriched by fluorescence- or magnetism-activated cell sorting and expanded by antigen stimulation or stimulation with CD3/CD28 antibodies or antibody-coated microbeads.

In some embodiments of the invention, an expression vector encoding the CD19-or-CD20 CAR is provided, where the vector may be a lentiviral vector, a retroviral vector, an adenoviral vector, an adeno-associated viral vector, a plasmid, or RNA.

In some embodiments, a method of killing a cancer cell in an individual is provided, comprising the step of providing to the individual a therapeutically effective amount of a therapeutic cell of the invention, including an effector cell, such as a T cell, NK cell, NKT cell, etc., for example. The individual may have a B-cell malignancy, expressing on or both of CD20 and CD19. Any method of the invention may further comprise the step of delivering to the individual an additional cancer therapy, such as surgery, radiation, hormone therapy, chemotherapy, immunotherapy, or a combination thereof, for example.

In embodiments of the invention, a kit is provided comprising cells comprising a CD19-or-CD20 CAR and/or expression vector encoding a CD19-or-CD20 CAR.

BRIEF DESCRIPTION OF THE DRAWINGS

For a more complete understanding of the present invention, reference is now made to the following descriptions taken in conjunction with the accompanying drawing.

DETAILED DESCRIPTION OF THE EMBODIMENTS

Figure 1:
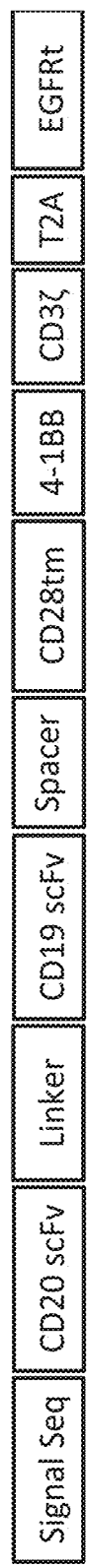
FIG. 1. Schematic of bispecific, CD20-OR-CD19 CAR. The bispecific CAR is composed of (from N to C terminal): A signal sequence that directs CAR localization to the cell membrane, the CD20 scFv, a peptide linker (e.g., (G4S)1, (G4S)3, SEQ ID NO:1 (EAAAK)1, or SEQ ID NO:1 (EAAAK)3), the CD19 scFv, followed by a spacer (e.g., the IgG4 hinge domain), a transmembrane domain (e.g., the transmembrane domain of CD28), one or more co-stimulatory domains (e.g., the cytoplasmic domain of 4-1BB or CD28), and the cytoplasmic domain of CD3 ζ chain. To facilitate identification of CAR-expressing T cells by antibody staining, truncated epidermal growth factor receptor (EGFRt) can be linked to the CAR via a self-cleaving peptide (e.g., T2A).

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

The term "genetic modification" means any process that adds, deletes, alters, or disrupts an endogenous nucleotide sequence and includes, but is not limited to viral mediated gene transfer, liposome mediated transfer, transformation, transfection and transduction, e.g., viral mediated gene transfer such as the use of vectors based on DNA viruses such as lentivirus, adenovirus, retroviruses, adeno-associated virus and herpes virus.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

"Antibody-dependent cell-mediated cytotoxicity" and "ADCC" refer to a cell-mediated reaction in which nonspecific cytotoxic cells that express Fc receptors, such as natural killer cells, neutrophils, and macrophages, recognize bound antibody on a target cell and cause lysis of the target cell. ADCC activity may be assessed using methods, such as those described in U.S. Pat. No. 5,821,337.

"Effector cells" are leukocytes which express one or more constant region receptors and perform effector functions.

To "treat" a disease or a disorder, such as cancer, means to take either therapeutic measures or preventative measures to lessen or abate the disease or disorder. Such treatment includes prevention, alleviation of symptoms, diminishment or stabilization of scope, and/or remission.

The term "therapeutically effective amount" refers to an amount of a compound or molecule effective to treat a disease or disorder.

"Cancer" refers to cells undergoing uncontrolled cellular growth. Examples of cancer include colorectal cancer and head and neck cancer. A "chemotherapeutic agent" is a chemical compound useful in the treatment of cancer.

A "cytokine" is a protein released by one cell to act on another cell as an intercellular mediator.

"Non-immunogenic" refers to a material that does not initiate, provoke or enhance an immune response where the immune response includes the adaptive and/or innate immune responses.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "vector" may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. Transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

"Receptor" means a polypeptide that is capable of specific binding to a molecule. Whereas many receptors may typically operate on the surface of a cell, some receptors may bind ligands when located inside the cell (and prior to transport to the surface) or may reside predominantly intracellularly and bind ligand therein.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab')$_2$, Fab, Fv, rIgG, and scFv fragments. The term scFv refers to a single chain Fv antibody in which the variable domains of the heavy chain and of the light chain of a traditional two chain antibody have been joined to form one chain.

The use of a single chain variable fragment (scFv) is of particular interest. scFvs are recombinant molecules in which the variable regions of light and heavy immunoglobulin chains encoding antigen-binding domains are engineered into a single polypeptide. Generally, the $V_H$ and $V_L$ sequences are joined by a linker sequence. See, for example, Ahmad (2012) Clinical and Developmental Immunology Article ID 980250, herein specifically incorporated by reference.

The length of the DNA linker used to link both of the domains is important for proper folding. It has been estimated that the peptide linker must span 3.5 nm (35 A) between the carboxy terminus of the variable domain and the amino terminus of the other domain without affecting the ability of the domains to fold and form an intact antigen-binding site. Many such linkers are known in the art, for example flexible linkers comprising stretches of Gly and Ser residues. The linkers used in the present invention include, without limitation, a rigid linker. In some specific embodiments of the invention, a rigid linker has the sequence SEQ ID NO:1 (EAAAK)n, where n is 1, 2, 3, 4, 5, 6, etc. In some specific embodiments, n is 3.

Spacer. A spacer region links the antigen binding domain to the transmembrane domain. It should be flexible enough to allow the antigen binding domain to orient in different directions to facilitate antigen recognition. The simplest form is the hinge region from an immunoglobulin, e.g. the hinge from any one of IgG1, IgG2a, IgG2b, IgG3, IgG4, particularly the human protein sequences. Alternatives include the $CH_2CH_3$ region of immunoglobulin and portions of CD3. For many scFv based constructs, an IgG hinge is effective.

T2A peptide. T2A peptide can be used to link the CAR of the invention to an epitope tag or other protein or peptide, including without limitation a sortable tag. T2A-linked multicistronic vectors can be used to express multiple proteins from a single open reading frame. The small T2A peptide sequences, when cloned between genes, allow for efficient, stoichiometric production of discrete protein products within a single vector through a novel "cleavage" event within the T2A peptide sequence. Various 2A peptide sequences are known and used in the art, for example see Szymczak-Workman et al. (2012) Cold Spring Harb Protoc. 2012(2):199-204, herein specifically incorporated by reference. They are small (18-22 amino acids) and have divergent amino-terminal sequences, which minimizes the chance for homologous recombination and allows for multiple, different 2A peptide sequences to be used within a single vector.

As used herein, the term "tumor microenvironment" refers to any and all elements of the tumor milieu that creates a structural and or functional environment for the malignant process to survive and/or expand and/or spread.

CD20 is a cell surface protein present on most B-cell neoplasms, and absent on otherwise similar appearing T-cell neoplasms. CD20 positive cells are also sometimes found in cases of Hodgkins disease, myeloma, and thymoma. CD20 is the target of the monoclonal antibodies (mAb) rituximab, ofatumumab, ocrelizumab, genmab, obinutuzumab, Ibritumomab tiuxetan, AME-133v, IMMU-106, TRU-015, and tositumomab, which are all active agents in the treatment of all B cell lymphomas and leukemias. For the purposes of the present invention, any of these antibodies may be converted into a scFv and used in the CAR. In some embodiments, the scFv is derived from Leu16 monoclonal antibody.

Cancers that may be treated with anti-CD20 reagents, e.g. antibodies and CARs, include without limitation B-cell lymphomas and leukemias, for example B-cell non-Hodgkin lymphomas (NHL), e.g. follicular lymphoma; hairy cell leukemia, and B-cell chronic lymphocytic leukemia (CLL). Anti-CD20 reagents are also useful in treating melanoma, e.g. targeting melanoma cancer stem cells.

CD19 expression is a hallmark of B cells. CD19 antigen is a type I transmembrane glycoprotein belonging to the immunoglobulin Ig superfamily. CD19 is specifically expressed in normal B cells and neoplastic B cells. It is considered a pan B-cell marker expressed throughout B-cell development but with threefold higher expression in mature cells as compared to immature B cells. CD19 expression however, is lost in the terminally differentiated plasma cells. During lymphopoiesis, CD19 directs B-cell fate and differentiation by modulating B-cell receptor signaling. It is critically involved in establishing the optimal immune response through its roles in the antigen-independent development as well as the immunoglobulin-induced activation of B cells. CD19 deficiency in humans and mice leads to an overall impaired humoral response with increased susceptibility to infection.

The pattern of CD19 expression is maintained among B-cell malignancies where it is expressed in indolent and aggressive subtypes of B cell lymphomas and leukemias, including NHL, B-cell CLL, and non-T acute lymphoblastic leukemia (ALL). CD19 is expressed in the B-cell lineage at an earlier stage compared with CD20. This fact therefore, may provide an advantage to CD19 targeted drugs over rituximab, especially for early B-cell neoplasms like acute lymphoblastic leukemia. Moreover, CD19 is shown to be internalized efficiently in lymphoma tumor models with the use of different monoclonal antibodies (huB4, hBU12). Various anti-CD19 antibodies can be formatted for use in the constructs of the present invention, including without limitation huB4, which is a humanized anti-CD19 antibody. In some embodiments of the invention, the anti-CD19 scFv is the FMC63 antibody.

Highly selective targeted T cell therapies are emerging as effective non-toxic modalities for the treatment of cancer. Malignancies are complex diseases where multiple elements contribute to the overall pathogenesis through both distinct and redundant mechanisms. Hence, targeting different cancer-specific markers simultaneously could result in better therapeutic efficacy. However, developing two separate cellular products for clinical use as combination therapy is impractical, owing to regulatory hurdles and cost. In contrast, rendering an individual T cell bispecific offsets tumor escape because of antigen loss.

In one embodiment, the bispecific CAR comprises a modified endogenous cell-surface molecule that may be used as a non-immunogenic selection epitope compatible with immunomagnetic selection. Non-immunogenic epitopes are those that normally do not raise an immune response in humans, and are usually proteins normally expressed in humans, or fragments thereof. Such a non-immunogenic selection epitope may facilitate immunotherapy in cancer patients without undesirable immunologic rejection of cell products. The endogenous cell surface molecule may be modified or truncated to retain an extracellular epitope recognized by a known antibody or functional fragment thereof, and to remove any signaling or trafficking domains and/or any extracellular domains unrecognized by said known antibody. A modified endogenous cell surface molecule which lacks a signaling or trafficking domain and/or any extracellular domains unrecognized by said known antibody is rendered inert. In some embodiments a truncated EGFR is used for this purpose.

The modified endogenous cell-surface molecule may be, but is not limited to, any non-immunogenic cell-surface related receptor, glycoprotein, cell adhesion molecule, antigen, integrin or cluster of differentiation (CD) that is modified as described herein. Modification of such cell-surface molecules is accomplished by keeping an epitope that is recognized by a known antibody or functional fragment thereof; and removing any signaling or trafficking domains and/or any extracellular domains unrecognized by a known antibody. Removal of the signaling or trafficking domains and/or any extracellular domains unrecognized by a known antibody renders the endogenous cell-surface molecule non-immunogenic and/or inert.

Thus, embodiments of the invention utilize an OR gate CAR as an artificial molecule that enables immune cells (T cells) to specifically and distinctly recognize and attack two cancer target molecules simultaneously, or to attack a cancer cell that has lost expression of either CD20 or CD19. The CAR is an artificial molecule that can be grafted onto T cells using genetic engineering technology to render them specific to a target of interest. This ability has substantial therapeutic implications, in that escape from single activity CARs has been reported.

The CAR architecture may be any suitable architecture, as known in the art. In certain embodiments, a cytoplasmic signaling domain, such as those derived from the T cell receptor ζ-chain, is employed as at least part of the chimeric receptor in order to produce stimulatory signals for T lymphocyte proliferation and effector function following engagement of the chimeric receptor with the target antigen. Examples would include, but are not limited to, endodomains from co-stimulatory molecules such as CD28, 4-1BB, and OX40 or the signaling components of cytokine receptors such as IL7 and IL15. In particular embodiments, co-stimulatory molecules are employed to enhance the activation, proliferation, and cytotoxicity of T cells produced by the CAR after antigen engagement. In specific embodiments, the co-stimulatory molecules are CD28, OX40, and 4-1BB and cytokine and the cytokine receptors are IL7 and IL15. The CAR may be first generation, second generation, or third generation CAR, in which signaling is provided by CD3 together with co-stimulation provided by CD28 and a tumor necrosis factor receptor (TNFr), such as 4-1BB or OX40), for example.

Embodiments of the invention include cells that express an OR-gate CAR of the invention. The cell may be of any kind, including an immune cell capable of expressing the OR-gate CAR of the invention for cancer therapy or a cell, such as a bacterial cell, that harbors an expression vector that encodes the OR-gate CAR of the invention. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T cells or killer T cell); NK cells and NKT cells are also encompassed in the invention.

The cells can be autologous cells, syngeneic cells, allogeneic cells and even in some cases, xenogeneic cells. In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

By way of illustration, cancer patients or patients susceptible to cancer or suspected of having cancer may be treated as follows. Cancers include particularly B-cell leukemias and lymphomas. CTLs modified as described herein may be administered to the patient and retained for extended periods of time. The individual may receive one or more administrations of the cells. In some embodiments, the genetically modified cells are encapsulated to inhibit immune recognition and placed at the site of the tumor. The cells may be injected at the tumor site or injected intravenously, for example.

In particular cases the individual is provided with therapeutic CTLs modified to comprise an OR-gate CAR of the invention. The cells may be delivered at the same time or at different times as another type of cancer therapy. The cells may be delivered in the same or separate formulations as another type of cancer therapy. The cells may be provided to the individual in separate delivery routes as another type of cancer therapy. The cells may be delivered by injection at a tumor site or intravenously or orally, for example. Routine delivery routes for such compositions are known in the art.

Expression vectors that encode the OR-gate CAR of the invention can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or *Herpes simplex* virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, one can knock-out an endogenous gene and replace it (at the same locus or elsewhere) with the gene encoded for by the construct using materials and methods as are known in the art for homologous recombination. For homologous recombination, one may use either omega or O-vectors. Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

The CTLs that have been modified with the construct(s) are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, including humans, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The cells may be administered as desired. Depending upon the response desired, the manner of administration, the life of the cells, the number of cells present, various protocols may be employed. The number of administrations will depend upon the factors described above at least in part.

In some embodiments AAV, retroviral or lentiviral vectors are used to deliver the OR-gate CAR of the invention to a T cell.

Adeno associated virus (AAV) is an attractive vector system for use in the cells of the present invention as it has a high frequency of integration and it can infect nondividing cells, thus making it useful for delivery of genes into mammalian cells, for example, in tissue culture or in vivo. AAV has a broad host range for infectivity. Details concerning the generation and use of rAAV vectors are described in U.S. Pat. Nos. 5,139,941 and 4,797,368, each incorporated herein by reference.

Retroviruses are useful as delivery vectors because of their ability to integrate their genes into the host genome, transferring a large amount of foreign genetic material, infecting a broad spectrum of species and cell types and of being packaged in special cell lines.

Lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2 and the Simian Immunodeficiency Virus: SIV. Recombinant lentiviral vectors are capable of infecting non-dividing cells and can be used for both in vivo and ex vivo gene transfer and expression of nucleic acid sequences. In some embodiments the lentiviral vector is a third generation vector (see, for example, Dull et al. (1998) J Virol. 72(11):8463-71). Such vectors are commercially available.

2nd generation lentiviral plasmids utilize the viral LTR promoter for gene expression, whereas 3rd-generation transfer vectors utilize a hybrid LTR promoter, see, for example Addgene for suitable vectors.

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means. Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references cited in this specification are hereby incorporated by reference in their entirety. The following examples are solely for the purpose of illustrating one embodiment of the invention.

Experimental Bispecific CD20-or-CD19 CAR

A bispecific CAR was constructed to have, from N to C terminal, a signal sequence that directs CAR localization to the cell membrane, the CD20 scFv, a peptide linker, the CD19 scFv, followed by a spacer (e.g., the IgG4 hinge domain), a transmembrane domain (e.g., the transmembrane domain of CD28), none or one or more co-stimulatory domains (e.g., the cytoplasmic domain of 4-1BB or CD28), and the cytoplasmic domain of CD3ζ chain. To facilitate identification of CAR-expressing T cells by antibody staining, truncated epidermal growth factor receptor (EGFRt) can be linked to the CAR via a self-cleaving peptide (e.g., T2A).

The amino acid sequence of various components is as follows:

```
GMpCSF signal sequence,
                                            (SEQ ID NO: 2)
METDTLLLWVLLLWVPGSTG CD20 scFv
                                            (SEQ ID NO: 3)
DIVLTQSPAILSASPGEKVTMTCRASSSVNYMDWYQKKPGSSPKPWIYAT

SNLASGVPARFSGSGSGTSYSLTISRVEAEDAATYYCQQWSFNPPTFGGG

TKLEIKGSTSGGGSGGGSGGGGSSEVQLQQSGAELVKPGASVKMSCKASG

YTFTSYNMHWVKQTPGQGLEWIGAIYPGNGDTSYNQKFKGKATLTADKSS

STAYMQLSSLTSEDSADYYCARSNYYGSSYWFFDVWGAGTTVTVSS

CD19 scFv
                                            (SEQ ID NO: 4)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGSTSGSGKPGSGEGSTKGEVKLQESGPGLVAPSQSLSVTCTVS

GVSLPDYGVSWIRQPPRKGLEWLGVIWGSETTYYNSALKSRLTIIKDNSK

SQVFLKMNSLQTDDTAIYYCAKHYYYGGSYAMDYWGQGTSVTVSS

IgG4 Hinge
                                            (SEQ ID NO: 5)
ESKYGPPCPPCP CD28 transmembrane domain
                                            (SEQ ID NO: 6)
MFWVLVVVGGVLACYSLLVTVAFIIFWV CD28 cytoplasmic domain
                                            (SEQ ID NO: 7)
RSKRSRGGHSDYMNMTPRRPGPTRKHYQPYAPPRDFAAYRS 4-1BB cytoplasmic domain
                                            (SEQ ID NO: 8)
KRGRKKLLYIFKQPFMRPVQTTQEEDGCSCRFPEEEEGGCEL
```

CD3ζ cytoplasmic domain
(SEQ ID NO: 9)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

T2A self-cleaving peptide
(SEQ ID NO: 10)
LEGGGEGRGSLLTCGDVEENPGPR

IgG4 CH2
(SEQ ID NO: 11)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK

IgG4 CH3
(SEQ ID NO: 12)
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK

Truncated epidermal growth factor receptor (EGFRt)
(SEQ ID NO: 13)
MLLLVTSLLLCELPHPAFLLIPRKVCNGIGIGEFKDSLSINATNIKHFKN

CTSISGDLHILPVAFRGDSFTHTPPLDPQELDILKTVKEITGFLLIQAWP

ENRTDLHAFENLEIIRGRTKQHGQFSLAVVSLNITSLGLRSLKEISDGDV

IISGNKNLCYANTINWKKLFGTSGQKTKIISNRGENSCKATGQVCHALCS

PEGCWGPEPRDCVSCRNVSRGRECVDKCNLLEGEPREFVENSECIQCHPE

CLPQAMNITCTGRGPDNCIQCAHYIDGPHCVKTCPAGVMGENNTLVWKYA

DAGHVCHLCHPNCTYGCTGPGLEGCPTNGPKIPSIATGMVGALLLLLVVA

LGIGLFM

Figures 2A, 2B:
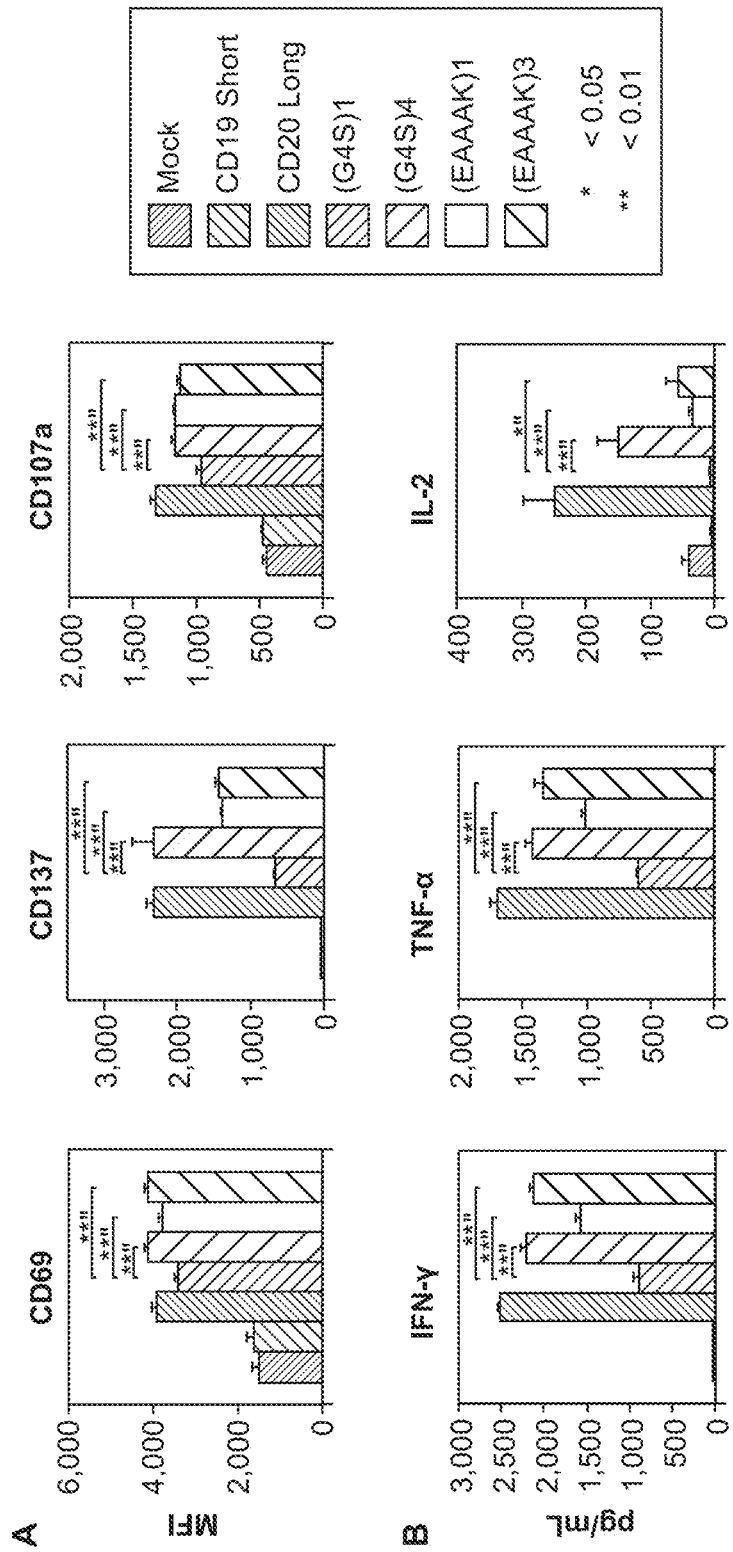
FIG. 2A-2B. OR-gate CARs but not single-input CD19 CARs respond to Raji lymphoma cells that have undergone antigen escape. (A) CD69, CD137, and CD107a surface expression (in median fluorescence intensity; MFI) by CAR-T cells after a 24-hour co-incubation with CD19− Raji cells. (B) IFN-γ, TNF-α, and IL-2 production by the CAR-T cells in (A) as measured by cytometric bead array assay. Mock: T cells that have been mock transduced and do not express CARs. CD19 Short: single-input CD19 CAR with IgG4 hinge as spacer. CD20 Long: single-input CD20 CAR with IgG4 hinge-CH2-CH3 as spacer. (G4S)1, (G4S)4, SEQ ID NO:1 (EAAAK)1, and SEQ ID NO:1 (EAAAK)3 indicate the linker sequence of CD20-OR-CD19 CARs, all of which contain the IgG4 hinge as spacer. Reported values are the mean of triplicates, with error bars indicating one standard deviation. P-values were calculated by two-tailed Student's t test; *: p<0.05; **: p<0.01.

OR-gate CARs but not single-input CD19 CARs respond to Raji lymphoma cells that have undergone antigen escape, as shown in FIG. 2 by expression of CD69, CD137 and CD1-7a on the surface of the CAR-expressing T cells, and by the release of cytokines. The controls include a CD19 Short single-input CD19 CAR with IgG4 hinge as spacer; and CD20 Long single-input CD20 CAR with IgG4 hinge-CH2-CH3 as spacer. Various linkers were tested, including (G4S)1, (G4S)4, (SEQ ID NO:1, EAAAK)1, and (D NO:1, EAAAAK)3.

Figure 3:
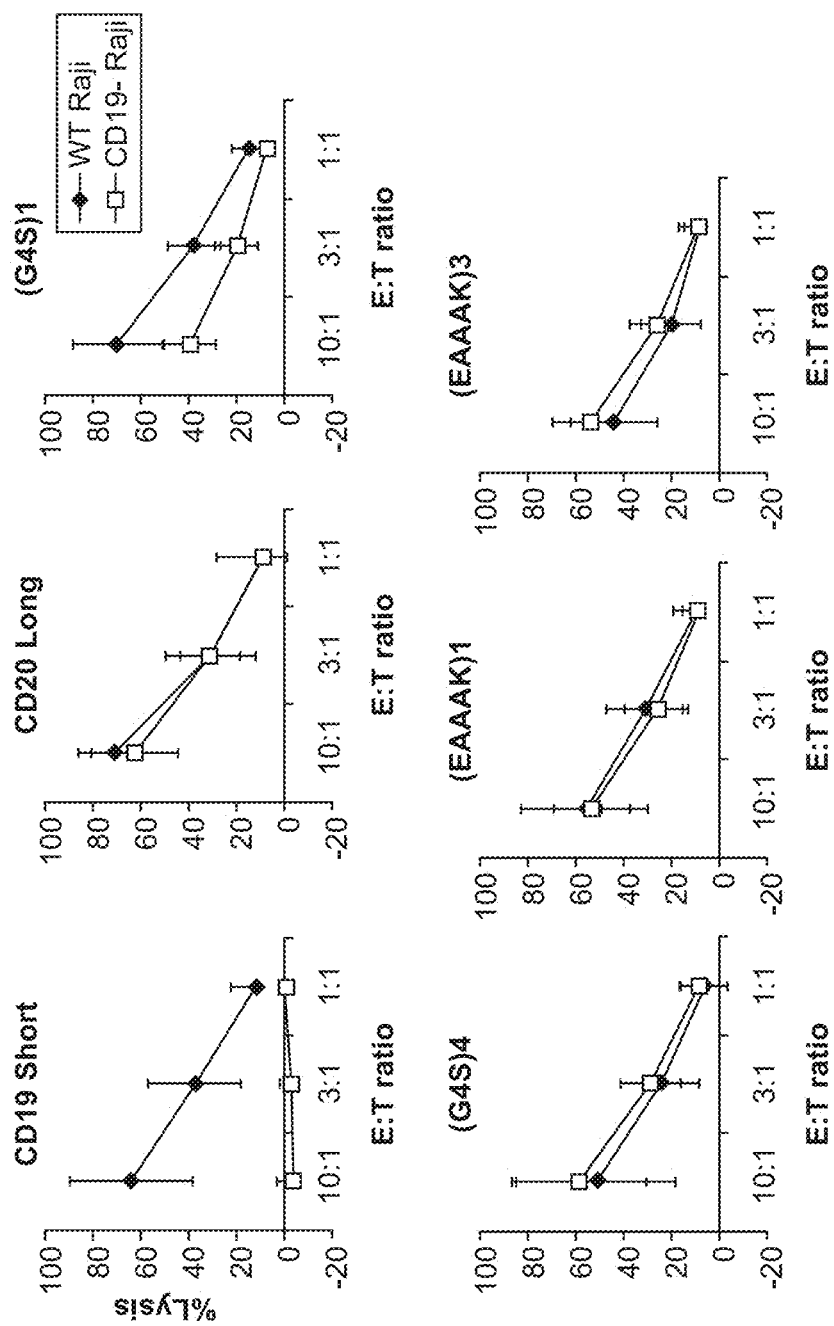
FIG. 3. Cell lysis by single-input and OR-gate CAR-T cells after 4-hour co-incubation with wildtype (WT; CD19+/CD20+) or CD19− Raji (CD19−/CD20+) cells. Reported values are the mean of triplicates, with error bars indicating one standard deviation. CAR identities are as described in FIG. 2.
Figures 4A, 4B:
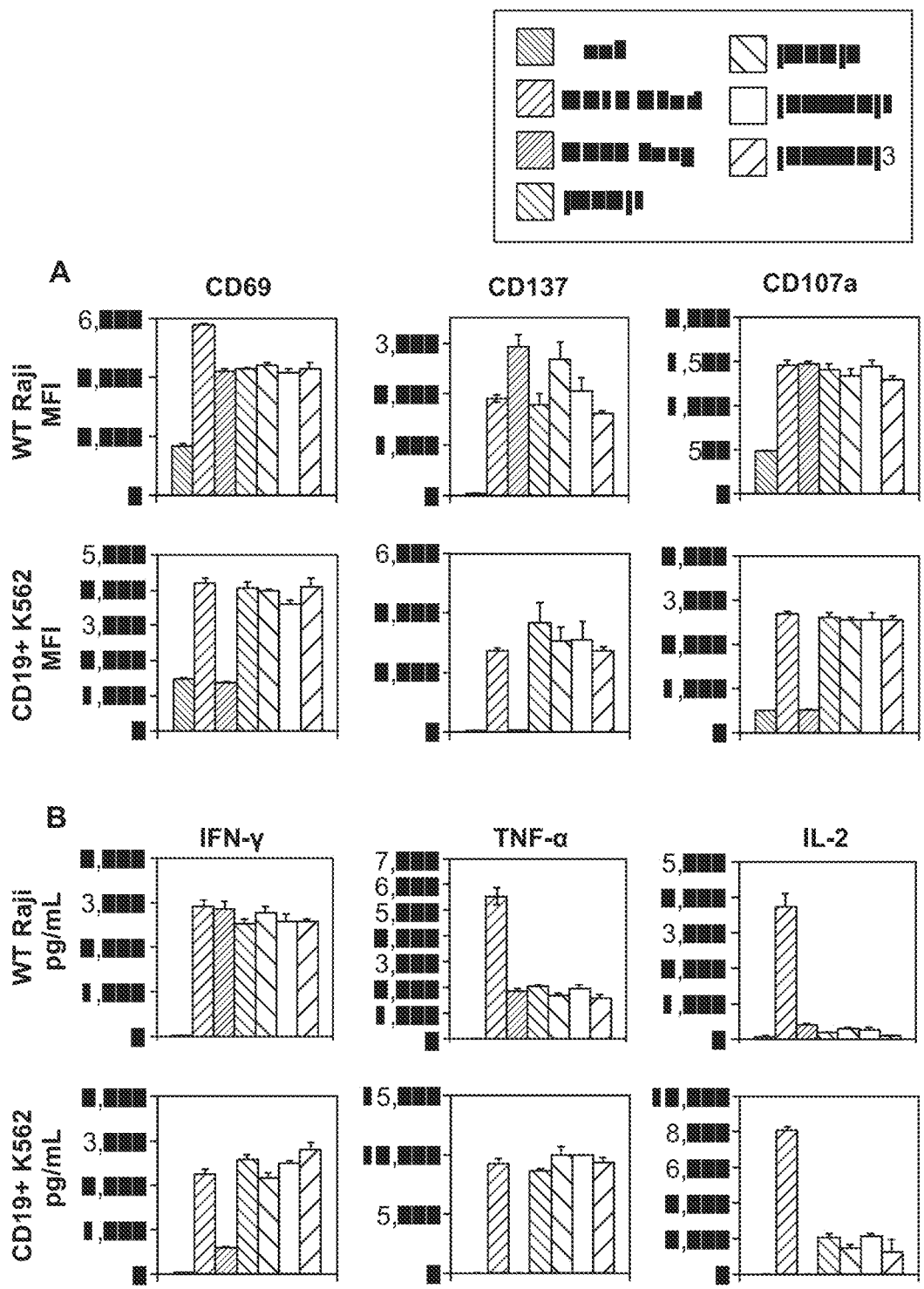
FIG. 4A-4B. Bispecificity is not compromised CD19 detection by OR-gate CARs. CAR-T cells were co-incubated with wildtype Raji or CD19+ K562 targets for 24 hours. (A) CD69, CD137, and CD107a surface expression was quantified by flow cytometry. (B) IFN-γ, TNF-α, and IL-2 production was quantified by cytometric bead array assay. Reported values are the mean of triplicates, with error bars indicating one standard deviation. CAR identities are as described in FIG. 2.

A comparison of cell lysis by single-input and OR-gate CAR-T cells after 4-hour co-incubation with wildtype (WT; CD19+/CD20+) or CD19− Raji (CD19−/CD20+) cells is shown in FIG. 3. The bispecificity was not compromised in OR-gate CARs. CAR-T cells were co-incubated with WT Raji or CD19+ K562 targets for 24 hours, and the expression of relevant activation-induced antigens and release of cytokines are shown in FIG. 4.

Figures 5A, 5B, 5C, 5D, 5E:
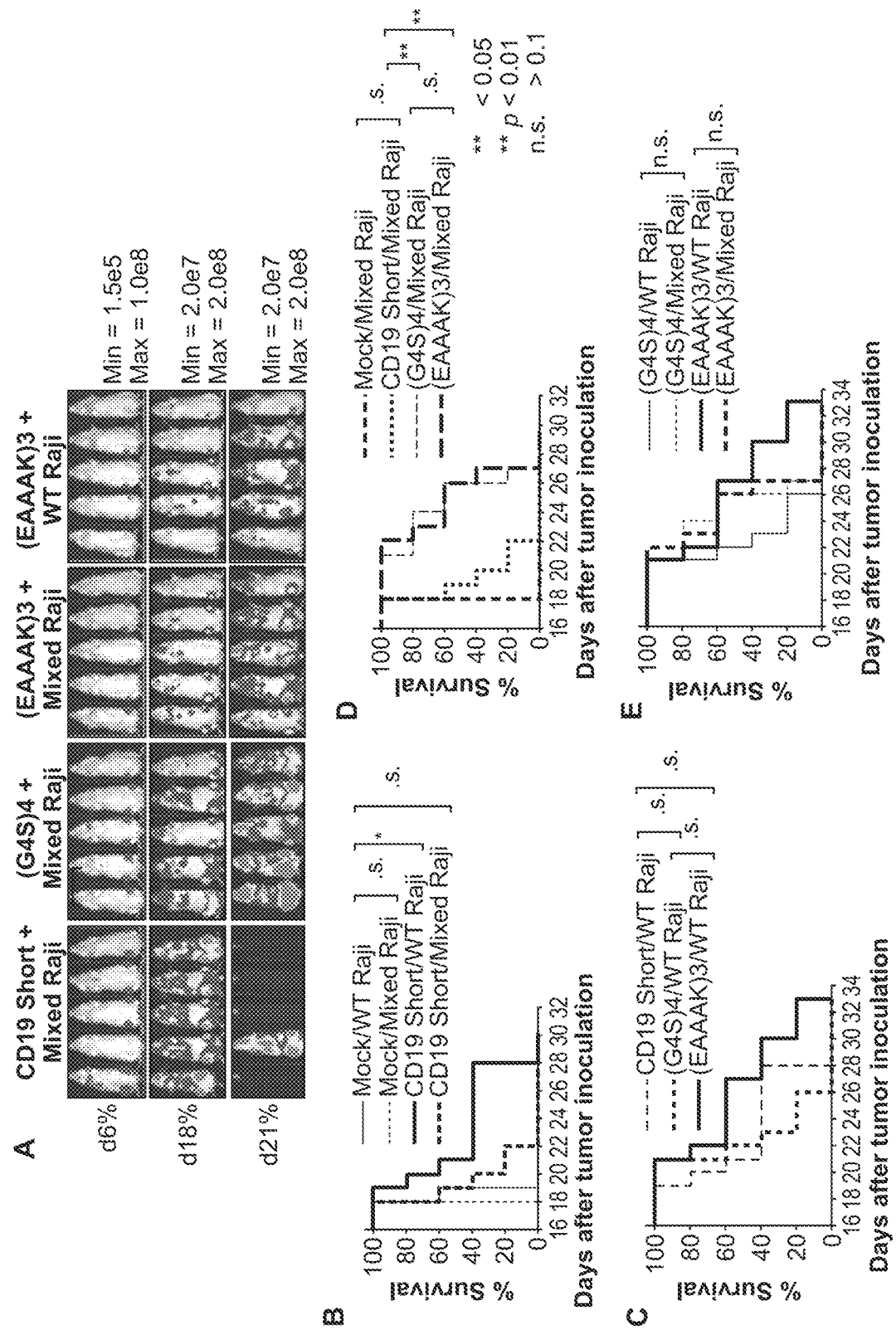
FIG. 5A-5E. OR-gate CARs abrogate the effects of antigen escape in vivo. (A) Tumor progression in NSG mice bearing wildtype (WT) or mixed (75% wildtype; 25% CD19−) Raji xenografts. Bioluminescence imaging was performed on days 6, 18, and 21 post tumor injection (T cells were injected on day 7). (B) Survival of mice bearing WT or mixed Raji tumor xenografts and treated with T cells expressing no CAR or the single-input CD19 CAR. Results indicate single-input CD19 CAR is able to significantly extend the survival of animals engrafted with WT Raji tumors. (C) Survival of mice bearing WT Raji tumor xenografts and treated with T cells expressing the single-input CD19 CAR or OR-gate CARs. Results indicate OR-gate CARs are as efficient as single-input CD19 CAR in targeting wildtype Raji lymphoma. (D) Survival of mice bearing mixed Raji tumor xenografts and treated with T cells expressing no CAR, the single-input CD19 CAR, or OR-gate CARs. Results indicate only OR-gate CARs are able to significantly extend survival of animals bearing CD19− mutant tumors. (E) Survival of mice bearing WT or mixed Raji tumor xenografts and treated with T cells expressing OR-gate CARs. Results indicate OR-gate CARs are equally efficient against WT and CD19− mutant Raji tumors, thus rendering the T cells insensitive to antigen loss by target cells. N=5 in all test groups. P-values were calculated by log-rank test analysis; n.s.: not significant (p>0.1); *: p<0.1; **: p<0.05. CAR identities are as described in FIG. 2.
Figure 6:
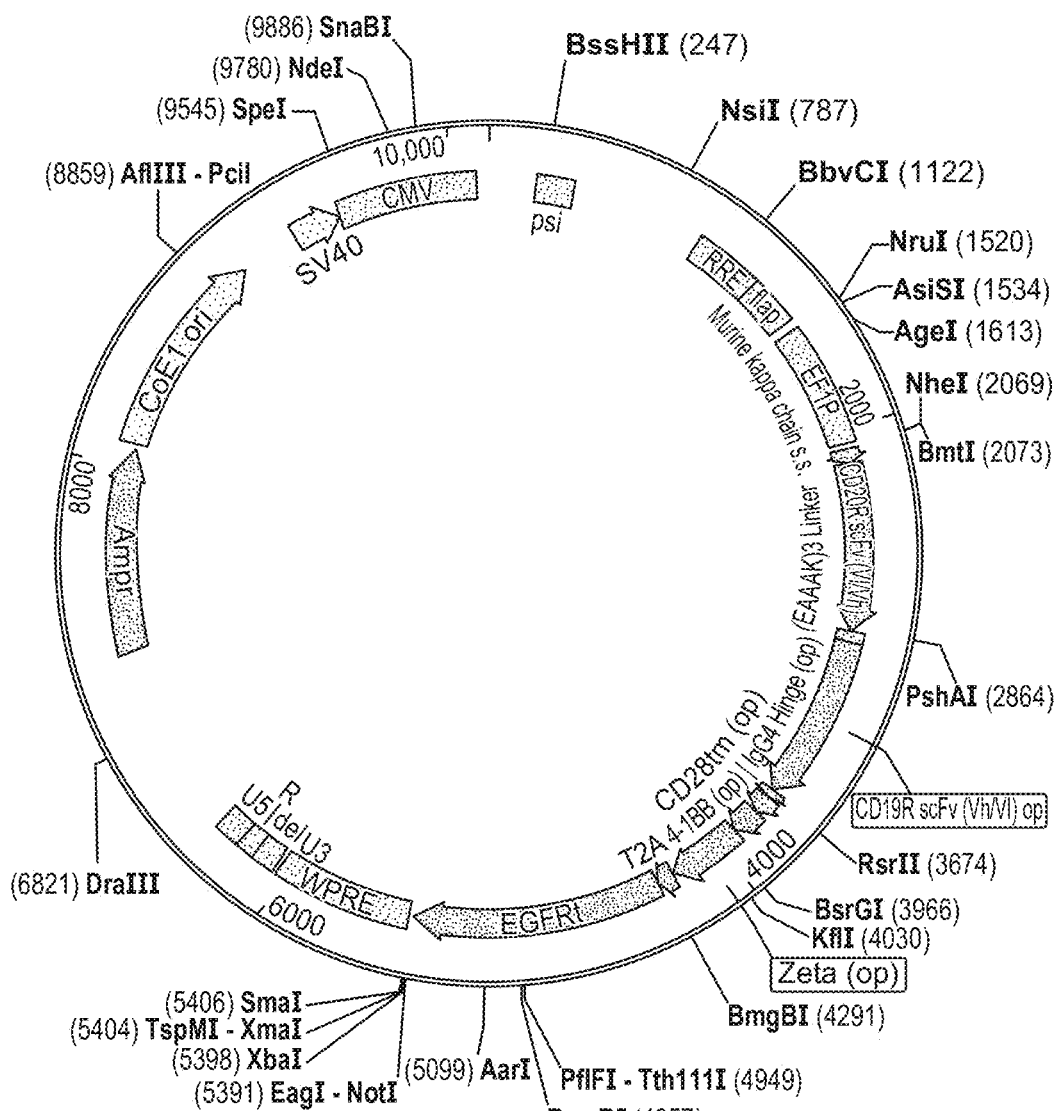
FIG. 6. Representative plasmid map of a bispecific, CD20-OR-CD19 CAR.

In vivo data, shown in FIG. 5, show OR-gate CARs abrogate the effects of antigen escape. In the survival of mice bearing WT or mixed Raji tumor xenografts and treated with T cells expressing no CAR or the single-input CD19 CAR, the results showed that single-input CD19 CAR was able to significantly extend the survival of animals engrafted with WT Raji tumors, and that OR-gate CARs are as efficient as single-input CD19 CAR in targeting WT Raji lymphoma. However, only OR-gate CARs were able to significantly extend survival of animals bearing CD19− mutant tumors. OR-gate CARs are equally efficient against WT and CD19− mutant Raji tumors, thus rendering the T cells insensitive to antigen loss by target cells.

What is claimed is:

1. A polypeptide comprising a CD19-OR-CD20 chimeric antigen receptor (CAR), comprising in order: anti CD20 scFv comprising a light chain variable region and heavy chain variable region from SEQ ID NO:3; (G4S)4 linker; anti-CD19 scFv comprising a heavy chain variable region and light chain variable region from SEQ ID NO:4; spacer domain of SEQ ID NO:5; transmembrane domain of SEQ ID NO:6; 4-1 BB cytoplasmic signaling domain of SEQ ID NO:8; CD3 zeta signaling domain of SEQ ID NO:9.

2. The polypeptide of claim 1, wherein the polypeptide further comprises a sortable tag.

3. A nucleic acid encoding a polypeptide according to claim 1.

4. A cell comprising the polypeptide of claim 1.

5. The cell of claim 4, wherein the cell is a T cell.

6. The polypeptide of claim 2, wherein the polypeptide further comprises a T2A cleavage site between the CAR and sortable tag.

7. The polypeptide of claim 6, wherein the T2A cleavage site comprises SEQ ID NO:10.

8. The polypeptide of claim 1, wherein the CAR consists of, in order: anti CD20 scFv having the light chain variable region and heavy chain variable region from SEQ ID NO:3; (G4S)4linker; anti-CD19 scFv having the heavy chain variable region and light chain variable region from SEQ ID NO:4; the spacer domain of SEQ ID NO:5; the transmembrane domain of SEQ ID NO:6; the 4-1 BB cytoplasmic signaling domain of SEQ ID NO:8; and the CD3 zeta signaling domain of SEQ ID NO:9.

9. The polypeptide of claim 1, wherein the polypeptide further comprises a signal sequence of SEQ ID NO:2.

10. A cell comprising the nucleic acid of claim 3.

* * * * *